United States Patent [19]

Christgau et al.

[11] Patent Number: 5,795,764
[45] Date of Patent: Aug. 18, 1998

[54] ENZYME EXHIBITING MANNANASE ACTIVITY

[75] Inventors: Stephan Christgau, Vedbaek; Lene Venke Kofod, Ugerloese; Lene Nonboe Andersen, Birkeroed; Sakari Kauppinen, Copenhagen; Hans Peter Heldt-Hansen; Henrik Dalboege, both of Virum, all of Denmark

[73] Assignee: Novo Nordisk A/S, Bagsvaerd, Denmark

[21] Appl. No.: 525,697

[22] PCT Filed: Apr. 28, 1994

[86] PCT No.: PCT/DK94/00174

§ 371 Date: Sep. 21, 1995

§ 102(e) Date: Sep. 21, 1995

[87] PCT Pub. No.: WO94/25576

PCT Pub. Date: Nov. 10, 1994

[30] Foreign Application Priority Data

Apr. 30, 1993 [DK] Denmark ................. 0486/93

[51] Int. Cl.⁶ .................. C12N 9/24; C12N 15/00; C12N 1/14; C07H 21/04
[52] U.S. Cl. .................. 435/200; 435/320.1; 435/252.3; 435/254.11; 435/254.3; 536/23.2
[58] Field of Search ................. 435/69.1, 252.3, 435/254.11, 277, 278, 281, 320.1, 200, 254.3; 536/23.2

[56] References Cited

FOREIGN PATENT DOCUMENTS

WO 91/18974  12/1991  WIPO.
WO 93/24622  12/1993  WIPO.

OTHER PUBLICATIONS

Christgau et al. (1994) Biochem. Mol. Biol. Int. 33(5): 917–925.
Murao et al. (1979) J. Ferment. Technol. 57(3): 151–156.
Harris, ELV (1989) In: Protein Purification Methods: A Practical Approach, Haris, ELV and S Angal, eds. IRL Press, Oxford.
Janson, J. (1984) Trends in Biotechnology 2(2): 31–38.
JP Abstract 63209586, Aug. 31, 1988, Derwent Database Week 8841.

Primary Examiner—Robert A. Wax
Assistant Examiner—Lisa J. Hobbs
Attorney, Agent, or Firm—Steve T. Zelson, Esq.; Valeta Gregg, Esq.

[57] ABSTRACT

An enzyme exhibiting mannanase activity, which enzyme i) is immunologically reactive with an antibody raised against a purified mannanase derived from *Aspergillus aculeatus*, CBS 101.43; ii) is encoded by the DNA sequences shown in SEQ ID No. 1 or an analogue of said sequence, and/or; iii) comprises the amino acid sequence shown in SEQ ID No. 2 or a sequence being an least 70% homologous thereto. The enzyme may be used for various purposes for which degradation or modification of a plant or algal cell wall material is desirable.

9 Claims, 4 Drawing Sheets

ENZYME EXHIBITING MANNANASE ACTIVITY

CROSS-REFERENCE TO RELATED APPLICATIONS

This application is a continuation of PCT/DK94/00174 filed Apr. 28, 1994, which is incorporated herein by reference.

FIELD OF INVENTION

The present invention relates to an enzyme with mannanase activity, a method of producing the enzyme, and an enzyme preparation containing the enzyme.

BACKGROUND OF THE INVENTION

Mannanases (EC 3.2.1.78) consitute a group of polysaccharases which degrade mannans. Mannan containing polysaccharides are a major component of the the hemicellulose fraction in both hardwoods and softwoods as well as in the endosperm in many leguminous seeds and in some mature seeds of non-leguminous plants (Dekker 1979; Araujo and Ward 1990). Essentially unsubstituted linear β-1,4-mannan is found in some non-leguminous plants (e.g. *Phytelepas macrocarpa*, or ivory nut). Unsubstituted β-1,4-mannan resembles cellulose in the conformation of the individual polysaccharide chains, and it is water insoluble. In leguminous seeds, water soluble galactomannan is the main storage carbohydrate, comprising up to 20% of the total dry weight in some cases (McCleary 1988). Galctomannan has α-galactose linked to O-6 of mannose residues and it can also be acetylated to various degrees on O-2 and O-3 of the mannose residues.

Mannans are also known from several monocotyledonous plants, and is found to be the most abundant polysaccharide in the cell walls material in palm kernel meal (Düsterhöft et al.; J. Sci. Food Agric 55 (1991) 411–422). Glucomannans are linear polysaccharides with more or less regularly alternating β-1,4 linked mannose and glucose. Glucomannans are found in e.g. konjac (*Amorphophallus konjac*).

Mannans, galactomannans, glucomannans and galactoglucomannans (glucomannans which galactose sidebranches) contributes more than 50% of the softwood hemicelluloses. Furthermore, the cellulose of many red algae contains a significant amount of mannose, e.g. the so-called α-cellulose from Porphyra is pure mannan.

Mannanases which are capable of cleaving glycosidic bonds in mannans, glucomannans, galactomannans and galactoglucomannans are useful enzymes within the food, oil, paper, and textile industry.

Mannases have been purified from a different sources (Dekker 1979). The majority of the β-mannanases which have been purified to homogeneity and/or cloned have been isolated from either prokaryots or from plants (Araujo and Ward 1990; Gibbs, Saul et al. 1992; Arcand, Kluepfel et al. 1993; Henrissat 1993). Fungal mannanases have been described by McCleary (1988) (an *Aspergillus niger* mannanase), Araujo and Ward (1990), and Johnson (1990).

WO 93/24622 published only after the priority date of the present invention describes a mannanase isolated from *Trichoderma reesei* and the DNA sequence encoding said mannanase.

SUMMARY OF THE INVENTION

It is an object of the present invention to prepare a single-component mannanase.

Accordingly, the present invention relates to an enzyme exhibiting mannanase activity, which enzyme i) is immunologically reactive with an antibody raised against a purified mannanase derived from *Aspergillus aculeatus*, CBS 101.43, ii) is encoded by the coding part of the DNA sequence shown in SEQ ID No. 1 or an analogue of said sequence, and/or iii) comprises the amino acid sequence shown in SEQ ID No. 2 or a sequence being at least 80% homologous thereto.

In the present context, the term "derived from" is intended not only to indicate a mannanase produced by strain CBS 101.43, but also a mannanase encoded by a DNA sequence isolated from strain CBS 101.43 and produced in a host organism transformed with said DNA sequence.

The term "analogue" is intended to indicate a DNA sequence which hybridizes with the same oligonucleotide probe as the DNA sequence shown in SEQ ID No. 1 under certain specified conditions (such as presoaking in 5×SSC and prehybridizing for 1 h at ~40° C. in a solution of 5×SSC, 5×Denhardt's solution, 50 mM sodium phosphate, pH 6.8, and 50 μg of denatured sonicated calf thymus DNA, followed by hybridization in the same solution supplemented with 50 μCi 32-P-dCTP labelled probe for 18 h at ~40° C. followed by washing three times in 2×SSC, 0.2% SDS at 40° C. for 30 minutes). Typically, the analogous DNA sequence is at least 70% homologous to the sequence shown in SEQ ID No. 1, such as at least 80% and preferably at least 85%, 90% or 95% homologous to any of these sequences. The term is intended to include modifications of the DNA sequence shown above, such as nucleotide substitutions which do not give rise to another amino acid sequence of the mannanase but which correspond to the codon usage of the host organism into which the DNA construct is introduced or nucleotide substitutions which do give rise to a different amino acid sequence and therefore, possibly, a different protein structure which might give rise to a mannanase mutant with different properties than the native enzyme. Other examples of possible modifications are insertion of one or more nucleotides into the sequence, addition of one or more nucleotides at either end of the sequence, or deletion of one or more nucleotides at either end or within the sequence.

The term "homologous" as used in connection with the polypeptide is intended to indicate the degree of identity with the amino acid sequence shown in SEQ ID No. 2, which may be determined by methods known in the art. Furthermore, the homologous polypeptide is prefereably one which is encoded by an analogue (as defined above) of the DNA sequence shown in SEQ ID No. 1.

In a further aspect, the invention relates to an enzyme exhibiting mannanase activity, which enzyme is encoded by a DNA sequence comprising the following partial sequence CTCGACACCA CCACACAACC AAGATGAAGC
TTTCTCACAT GCTCCTCAGC
CTCGCCAGCC TGGGGGTGGCG ACGGCTCTTC
CCCGGACGCC GAACCACAAC
GCGGCCACCA CCGCCTTCCC CAGCACCTCG
GGGCTGCACT TCACGATTGA
CGGCAAGACG GGCTACTTTG CCGGGACCAA
CTCGTACTGG ATCGGGTTCC
TGACCAACAA CGACGACGTG GACCTCGTCA
TGAGCCAGCT GGCGCAT (SEQ ID. No: 3)

or a sequence homologous thereto encoding a polypeptide with mannanase activity.

In a still further aspect, the invention relates to an enzyme exhibiting mannanase activity, which enzyme is encoded by a DNA sequence comprising at least one of the following partial sequences (a) CTCGACACCA CCACACAACC (SEQ ID. No: 4)
(b) AAGATGAAGC TTTCTCACAT (SEQ ID. No: 5)
(c) GCTCCTCAGC CTCGCCAGCC (SEQ ID. No: 6)
(d) TGGGGGTGGCG ACGGCTCTTC (SEQ ID. No: 7)
(e) CCCGGACGCC GAACCACAAC (SEQ ID. No: 8)
(f) GCGGCCACCA CCGCCTTCCC (SEQ ID. No: 9)
(g) CAGCACCTCG GGGCTGCACT (SEQ ID. No: 10)
(h) TCACGATTGA CGGCAAGACG (SEQ ID. No: 11)
(i) GGCTACTTTG CCGGGACCAA (SEQ ID. No: 12)
(j) CTCGTACTGG ATCGGGTTCC (SEQ ID. No: 13)
(k) TGACCAACAA CGACGACGTG (SEQ ID. No: 14)
(l) GACCTCGTCA TGAGCCAGCT GGCGCAT (SEQ ID. No: 15)

In a further aspect the invention relates to a DNA construct comprising a DNA sequence encoding an enzyme exhibiting mannanase activity, which DNA sequence comprises the coding part of the DNA sequence shown in SEQ ID No. 1 or is an analogue of said sequence, which a) hybridizes with an oligonucleotide probe prepared on the basis of the DNA sequence shown in SEQ ID No. 1, or any of the partial sequences shown above or of the amino acid sequence shown in SEQ ID No. 2, b) encodes a polypeptide comprising an amino acid sequence being at least 70%, such as at least 80%, 85% 90% or 95% homologous to the amino acid sequence shown in SEQ ID No. 2, and/or c) encodes a polypeptide which is immunologically cross-reactive with the polypeptide comprising the amino acid sequence shown in SEQ ID No. 2.

DETAILED DESCRIPTION OF THE INVENTION

Figure 1:
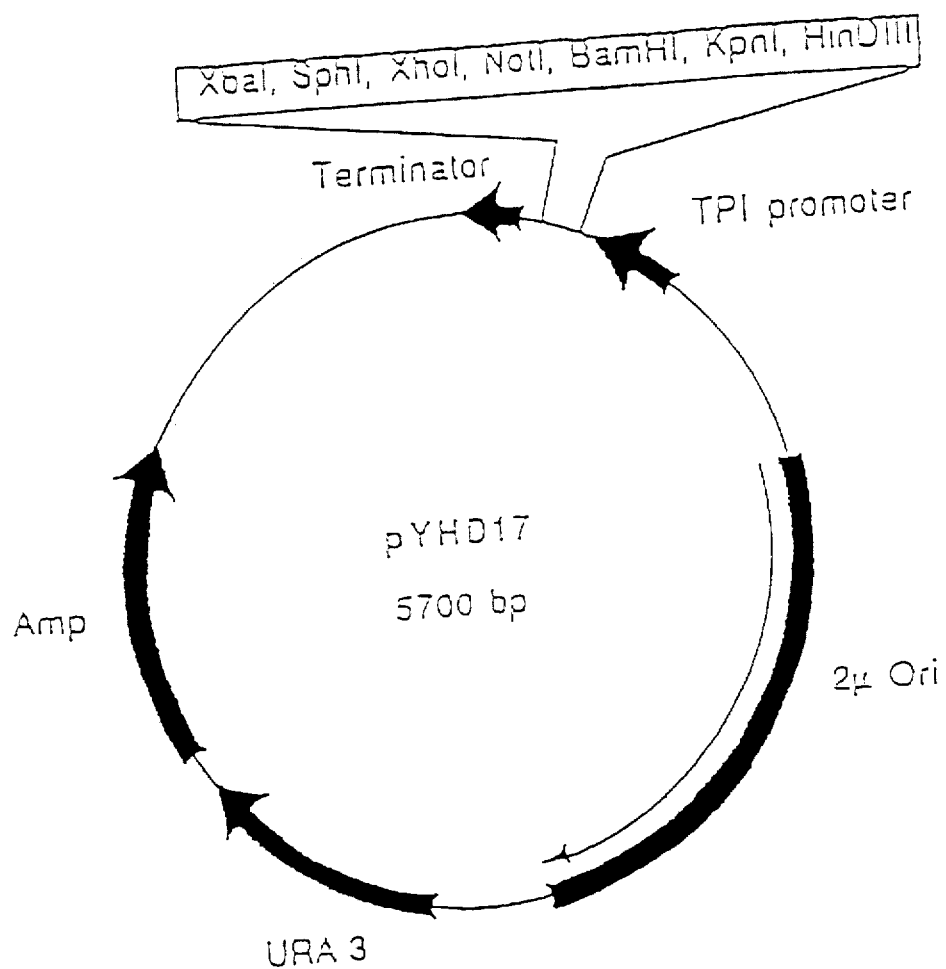

The enzyme of the invention may be isolated by a general method involving cloning, in suitable vectors, a DNA library from *Aspergillus aculeatus*, transforming suitable yeast host cells with said vectors, culturing the host cells under suitable conditions to express any enzyme of interest encoded by a clone in the DNA library, and screening for positive clones by determining any mannanase activity of the enzyme produced by such clones.

A more detailed description of this screening method is given in Example 1 below.

The DNA sequence coding for the enzyme may for instance be isolated by screening a cDNA library of *Aspergillus aculeatus*, e.g strain CBS 101.43, publicly available from the Centraalbureau voor Schimmelcultures, Delft, NL, and selecting for clones expressing the appropriate enzyme activity (i.e. mannanase activity as defined by the ability of the enzyme to hydrolyse glycosidic bonds in mannan. The appropriate DNA sequence may then be isolated from the clone by standard procedures, e.g. as described in Example 1. It is expected that DNA encoding a homologous enzyme may be isolated by similarly screening cDNA libraries of other microorganisms, in particular other Aspergillus sp. It is expected that a DNA sequence coding for a homologous enzyme may be derived by similarly screening a cDNA library of another microorganism, in particular a fungus, such as a strain of another Aspergillus sp., in particular a strain of *A. aculeatus*, *A. oryzae* or *A. niger*, a strain of a Trichoderma sp., in particular a strain of *T. harzianum*, or *T. reesei*, a strain of a Fusarium sp., in particular a strain of *F. oxysporum*, or a strain of a Humicola sp. or a strain of Scytallidium sp.

Alternatively, the DNA coding for a mannanase of the invention may, in accordance with well-known procedures, conveniently be isolated from DNA from any of the above mentioned organisms by use of synthetic oligonucleotide probes prepared on the basis of a DNA or amino acid sequence disclosed herein. For instance, a suitable oligonucleotide probe may be prepared on the basis of any of the partial nucleotide sequences (a)–(l) listed above.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the mannanase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the mannanase, the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y., 1989).

The host cell which is transformed with the DNA sequence encoding the enzyme of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of *Aspergillus oryzae* as a host microorganism is described in EP 238 023 (of Novo Nordisk A/S), the contents of which are hereby incorporated by reference. The host cell may also be a yeast cell, e.g. a strain of Saccharomyces, in particular *Saccharomyces cerevisiae*.

In a still further aspect, the present invention relates to a method of producing an enzyme according to the invention, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed mannanase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The thus purified mannanase may be employed for immunization of animals for the production of antibodies. More specifically, antiserum against the mannanase of the invention may be raised by immunizing rabbits (or other rodents) according to the procedure described by N. Axelsen et al. in: *A Manual of Quantitative Immunoelectroohoresis*, Blackwell Scientific Publications, 1973, Chapter 23, or A. Johnstone and R. Thorpe, *Immunochemistry in Practice*, Blackwell Scientific Publications, 1982 (more specifically pp. 27-31). Purified immunoglobulins may be obtained from the antisera, for example by salt precipitation (($NH_4)_2$ $SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al. Chapter 2).

In a still further aspect, the present invention relates to an enzyme preparation useful for the degradation of plant cell wall components, said preparation being enriched in an enzyme exhibiting mannanase activity as described above.

The enzyme preparation having been enriched with an enzyme of the invention may e.g. be an enzyme preparation comprising multiple enzymatic activities, in particular an enzyme preparation comprising multiple plant cell wall degrading enzymes such as Pectinex®, Pectinex Ultra SP®, Gamanase, Celluclast or Celluzyme (all available from Novo Nordisk A/S). In the present context, the term "enriched" is intended to indicate that the mannanase activity of the enzyme preparation has been increased, e.g. with an enrichment factor of at least 1.1, conveniently due to addition of an enzyme of the invention prepared by the method described above.

Alternatively, the enzyme preparation enriched in an enzyme exhibiting mannanase activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation of the invention may, in addition to a mannanase of the invention, contain one or more other plant cell wall degrading enzymes, for instance those with cellulytic, mannanolytic, xylanolytic or pectinolytic activities such as xylanase, α-galactosidase, β-mannosidase, xylan acetyl esterase, mannan acetyl esterase, arabinanase, rhamnogalacturonase, rhamnogalacturonan acetylesterase, pectin acetyl esterase, galactanase, polygalacturonase, pectin lyase, pectate lyase, glucanase or pectin methylesterase. The additional enzyme(s) may be producible by means of a microorganism belonging to the genus Aspergillus, preferably *Aspergillus niger*, *Aspergillus aculeatus*, *Aspergillus awamori* or *Aspergillus oryzae*, or Trichoderma.

The enzyme preparation according to the invention is preferably used as an agent for degradation or modification of plant and algal cell walls or any mannan-containing material originating from plant material.

Examples are given below of preferred uses of the enzyme preparation of the invention. The dosage of the enzyme preparation of the invention and other conditions under which the preparation is used may be determined on the basis of methods known in the art.

The mannanase of the invention hydrolyses β-1,4 linkages in mannans, glucomannans, galactomannans and galactoglucomannans. Mannans are polysaccharides having a backbone composed of β-1,4 linked mannose, glucomannans are polysaccharides having a backbone of more or less regularly alternating β-1,4 linked mannose and glucose. Galactomannans and Galactoglucomannans are mannans and glucomannans with α-1,6 linked galactose sidebranches. Mannans, glucomannans, galactomannans, and galactoglucomannans may be acetylated (as in softwood).

The degradation of galactomannan and galactoglucomannans mannanase is facilitated by full or partial removal of the galactose sidebranches. Further the degradation of acetylated mannans, glucomannans, galactoglucomannans and galactomannans is facilitated by a full or partial deacetylation. Acetyl groups can be removed by alkali or by mannan acetylesterases. The oligomers which are released by the mannanases or by a combination of mannanase and α-galactosidase and/or mannan acetyl esterase as mentioned above can be further degraded to free mannose by β-mannosidase and/or β-glucosidase.

The mannanase of the present invention can be used without other mannanolytic enzymes or with limited activity of other mannanolytic enzymes to degrade mannans, glucomannans, galactomannans, and galactoglucomannans for production of oligosaccharides. The oligosaccharides may be used as bulking agents, like galactomannan oligosaccharides released from e.g. guar gum and locust bean gum, mannan-oligomers released from palm seed mannan, or glucomannan oligosaccharides released with konjac glucomannan. The released oligosaccharides may be added to food, feed or beverage products as a bulking agent or stabilizer or in order to improve the intestinal flora.

The mannanase of the present invention can be used in combination with other mannanolytic enzymes to degrade mannans, glucomannans, galactoglucomannans and galactomannans to mannose and other monosaccharides.

The mannanase of the present invention may be used alone or together with other enzymes like glucanases and/or xylanases to improve the extraction of oil from oil-rich plant material, like extraction of palm oil, or palm kernel oil.

Mannan polymers are often present as a major contaminant in paper pulp, where it can be difficult to remove from the cellulose fibers. The mannanase of the invention may advantageously be used for removal or reduction of the amounts of these polymers.

Furthermore, the mannanase of the present invention may be used in the paper and pulp industry either alone or preferable together with xylanase(s), inter alia in the bleaching process to enhance the brightness of bleached pulps (fully or partially from softwood) whereby the amount of chlorine used in the bleaching stages may be reduced, and to increase the freeness of pulps in the recycled paper process (Eriksson, K. E. L., Wood Science and Technology 24 (1990): 79–101; Paice, et al., Biotechnol. and Bioeng. 32 (1988): 235–239 and Pommier et al., Tappi Journal (1989): 187–191). Furthermore, the mannanase alone or preferable in combination with xylanases may be used for treatment of lignocellulosic pulp (fully or partially from softwood) so as to improve the bleachability thereof. Thereby the amount of chlorine needed to obtain a satisfactory bleaching of the pulp may be reduced.

The mannanase of the invention may also be used in the preparation of fruit or vegetable juice like pine apple juice, e.g., in order to increase yield.

The mannanase of the invention may also be used to degrade plant and algal material in order to improve different kinds of processing, facilitate purification or extraction of other component than the mannans, galactomannans, galactoglucomannans, and glucomannans, like extraction or purification of carrageenan or other valuable components from red algae, where the mannanase preferable is used together with cellulases and/or xylanases.

Finally, the mannanase of the invention may be used in modifying the viscosity of plant derived material. For instance the mannanase may be used in the oil industry where guar gum and modified guar are used in, e.g., fracturing fluids and drilling muds. The mannanase can be used to clean oil wells, e.g. to break the high viscosity or gel structure in fractural fluid after the fracturation. The enzyme of the invention is contemplated to be of particular use for this purpose in that it has a high thermostability and thus may be resistant to the elevated temperatures in the ground. Further the mannanases can be used to treat used drill mud.

Another example is the textile industry where galactomannan or modified galactomannans are used in textile dyes. The removal of excess dye from the textile after the textile dying is facilitated by degradation of the galactomannan or modified galactomannan by the mannanase of the invention.

The invention is further described in the accompanying drawing in which

Figure 2:
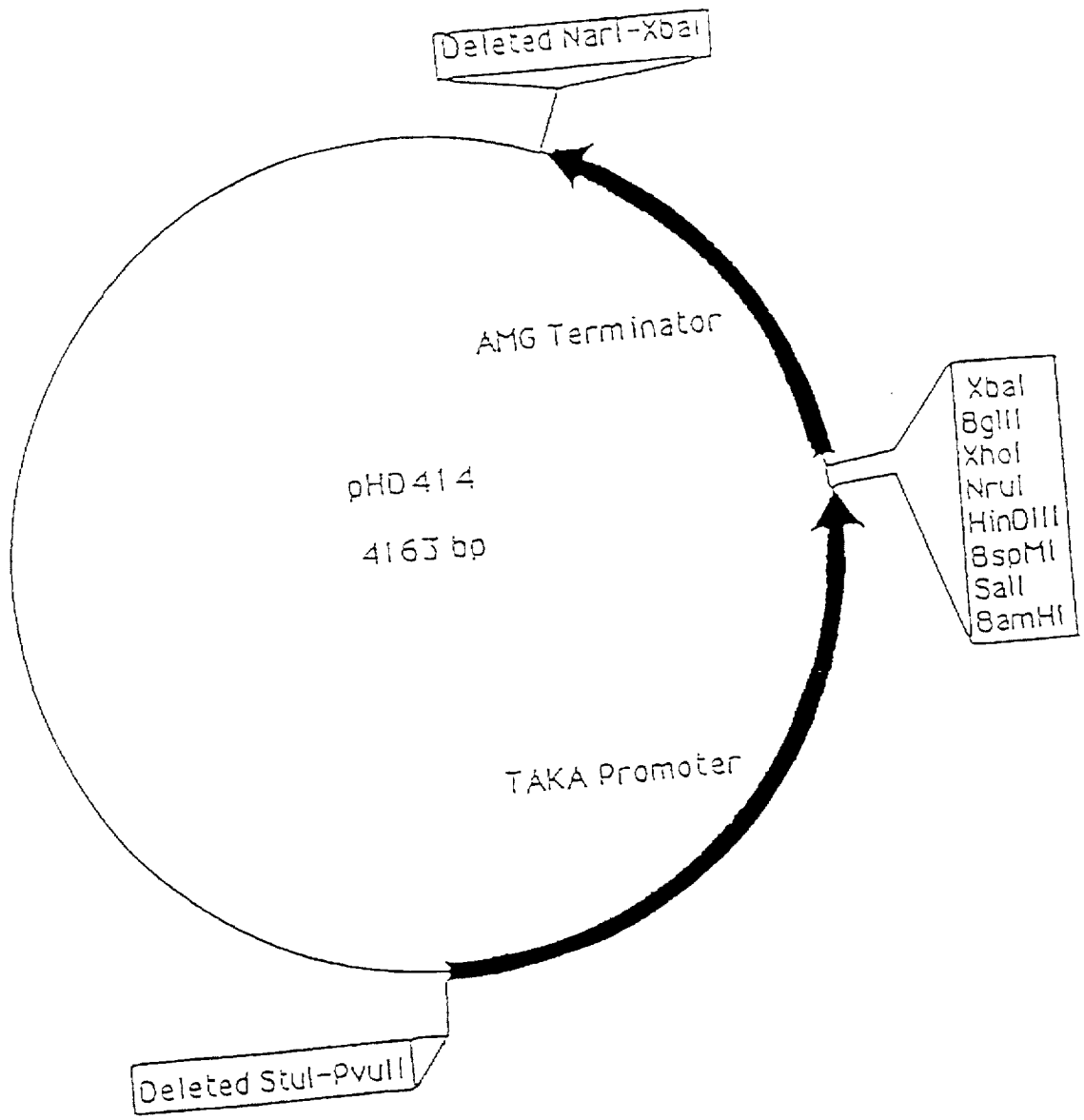
Figure 3:
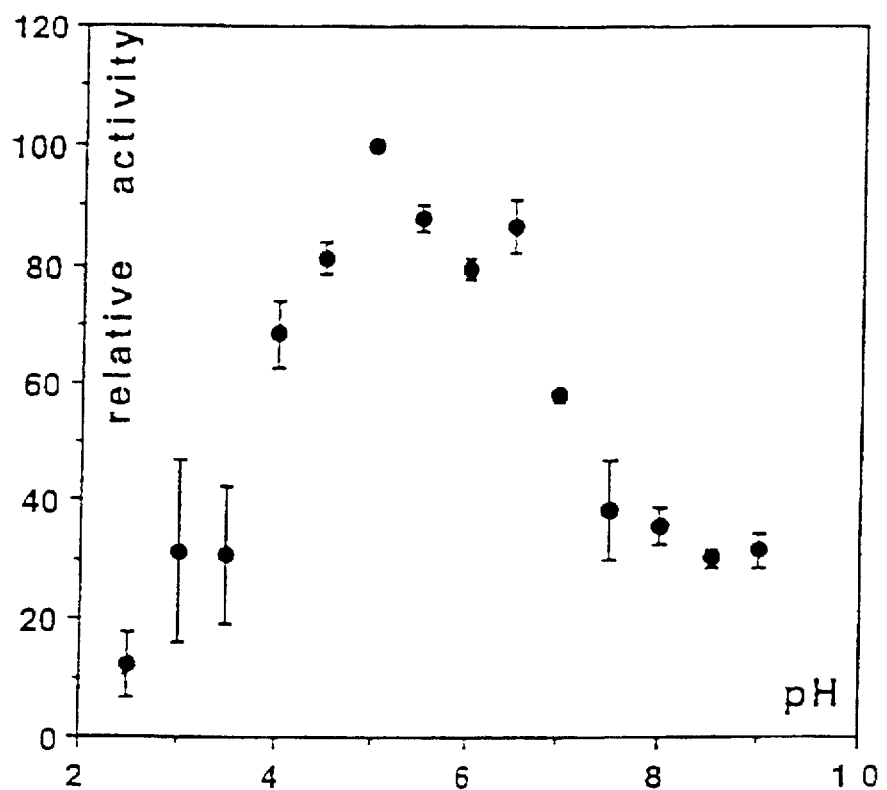

FIG. 1 is a restriction map of plasmid pYHD17,

FIG. 2 a restriction map of plasmid pHD 414,

FIG. 3 a pH optimum curve, and

Figure 4:
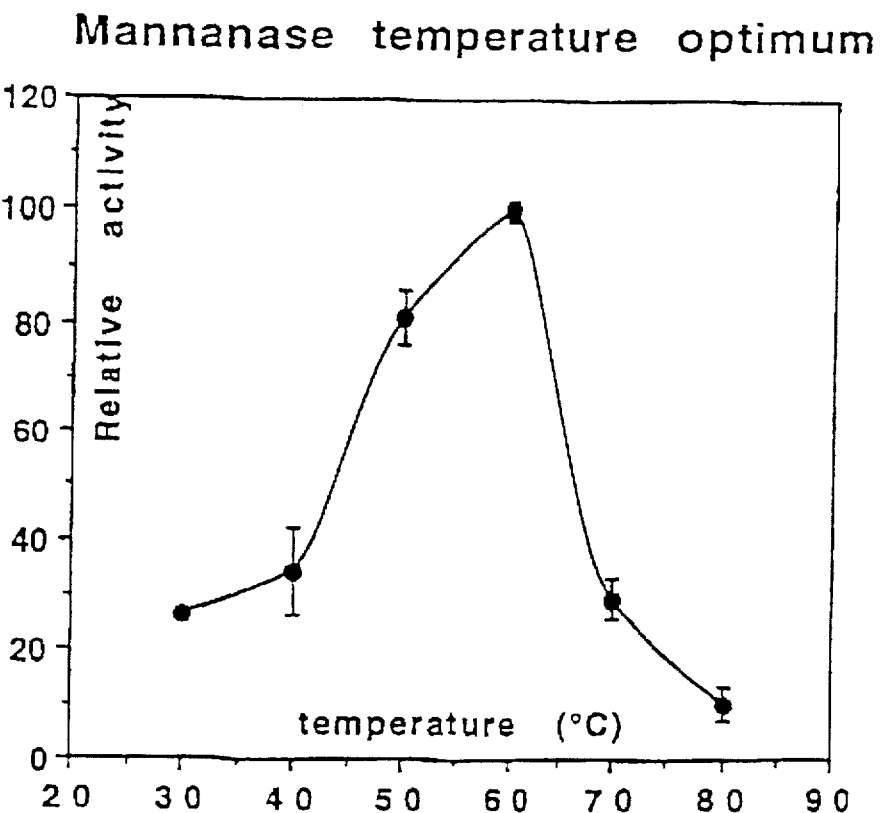

FIG. 4 a temperature optimum curve.

The invention is described in further detail in the following examples which are not in any way intended to limit the scope of the invention as claimed.

EXAMPLES

Materials and Methods

Donor organism mRNA was isolated from *Aspergillus aculeatus*, CBS 101.43, grown in a soy-containing fermentation medium with agitation to ensure sufficient aeration. Mycelia were harvested after 3-5 days' growth, immediately frozen in liquid nitrogen and stored at −80° C.

Yeast strains

The *Saccharomyces cerevisiae* strain used was yNG231 (MAT alpha, leu2, ura3-52, his4-539, pep4-delta 1, cir+) or JG169 (MATα; ura 3-52; leu 2-3, 112; his 3-D200; pep 4-113; prc1::HIS3; prb1:: LEU2; cir+).

Construction of an expression plasmid

The commercially available plasmid pYES II (Invitrogen) was cut with SpeI, filled in with Klenow DNA polymerase+ dNTP and cut with ClaI. The DNA was size fractionated on an agarose gel, and a fragment of about 2000 bp was purified by electroelution. The same plasmid was cut with ClaI/ PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, *J. Mol. Appl. Genet.* 1, 1982, pp. 419–434) was slightly modified: an internal SphI site was removed by deleting the four bp constituting the core of this site. Furthermore, redundant sequences upstream of the promoter were removed by BalI exonuclease treatment followed by addition of a SphI linker. Finally, an EcoRI linker was added at position-10. After these modifications, the promoter is included in a SphI-EcoRI fragment. Its effeciency compared to the original promoter appears to be unaffected by the modifications. The resulting plasmid pYHD17 is shown in FIG. 1.

Preparation of RNase-free glassware, tips and solutions

All glassware used in RNA isolations was baked at +220° C. for at least 12 h. Eppendorf tubes, pipet tips and plastic columns were treated in 0.1% diethylpyrocarbonate (DEPC) in EtOH for 12 h, and autoclaved. All buffers and water (except Tris-containing buffers) were treated with 0.1% DEPC for 12 h at 37° C., and autoclaved.

Extraction of total RNA

The total RNA was prepared by extraction with guanidinium thiocyanate followed by ultracentrifugation through a 5.7M CsCl cushion (Chirgwin et al., 1979) using the following modifications. The frozen mycelia were ground in liquid $N_2$ to fine powder with a mortar and a pestle, followed by grinding in a precooled coffee mill, and immediately suspended in 5 vols of RNA extraction buffer (4M GUSCN, 0.5% Na-laurylsarcosine, 25 mM Na-citrate, pH 7.0, 0.1M β-mercaptoethanol). The mixture was stirred for 30 min. at RT° and centrifuged (30 min., 5000 rpm, RT°, Heraeus Megafuge 1.0 R) to pellet the cell debris. The supernatant was collected, carefully layered onto a 5.7M CsCl cushion (5.7M CsCl, 0.1M EDTA, pH 7.5, 0.1% DEPC; autoclaved prior to use) using 26.5 ml supernatant per 12.0 ml CsCl cushion, and centrifuged to obtain the total RNA (Beckman, SW 28 rotor, 25 000 rpm, RT°, 24 h). After centrifugation the supernatant was carefully removed and the bottom of the tube containing the RNA pellet was cut off and rinsed with 70% EtOH. The total RNA pellet was transferred into an Eppendorf tube, suspended in 500 μl TE, pH 7.6 (if difficult, heat occasionally for 5 min at 65° C.), phenol extracted and precipitated with ethanol for 12 h at −20 C. (2.5 vols EtOH, 0.1 vol 3M NaAc, pH 5.2). The RNA was collected by centrifugation, washed in 70% EtOH, and resuspended in a minimum volume of DEPC-DIW. The RNA concentration was determined by measuring $OD_{260/280}$.

Isolation of poly(A)⁺RNA

The poly(A)⁺ RNAs were isolated by oligo(dT)-cellulose affinity chromatography (Aviv & Leder, 1972). Typically, 0.2 g of oligo(dT) cellulose (Boehringer Mannheim) was preswollen in 10 ml of 1×column loading buffer (20 mM Tris-Cl, pH 7.6, 0.5M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA was heated at 65° C. for 8 min., quenched on ice for 5 min, and after addition of 1 vol 2×column loading buffer to the RNA sample loaded onto the column. The eluate was collected and reloaded 2–3 times by heating the sample as above and quenching on ice prior to each loading. The oligo(dT) column was washed with 10 vols of 1× loading buffer, then with 3 vols of medium salt buffer (20 mM Tris-Cl, pH 7.6, 0.1M NaCl, 1 mM EDTA, 0.1% SDS), followed by elution of the poly(A)⁺ RNA with 3 vols of elution buffer (10 mM Tris-Cl, pH 7.6, 1 mM EDTA, 0.05% SDS) preheated to +65° C., by collecting 500 μl fractions. The $OD_{260}$ was read for each collected fraction, and the mRNA containing fractions were pooled and ethanol precipitated at −20° C. for 12 h. The poly(A)⁺ RNA was collected by centrifugation, resuspended in DEPC-DIW and stored in 5–10 μg aliquots at −80° C.

Northern blot analysis

The poly(A)⁺ RNAs (5 μg/sample) from various mycelia were electrophoresed in 1.2 agarose-2.2M formaldehyde gels (Sambrook et al., 1989) and blotted to nylon membranes (Hybond-N, Amersham) with 10×SSC (Sambrook et al., 1989) as transfer buffer. Three random-primed (Feinberg & Vogelstein, 1983) $^{32}$p-labeled cDNA probes were used in individual hybridizations: 1) a 1.3 kb Not I-Spe I fragment for polygalacturonase I from *A. aculeatus*, 2) a 1.3 kb Not I-Spe I fragment encoding endoglucanase I from *A. aculeatus* and 3) a 1.2 kb Eag I fragment coding for galactanase I from *A. aculeatus*. Northern hybridizations were carried out in 5×SSC (Sambrook et al., 1989), 5×Denhardt's solution (Sambrook et al., 1989), 0.5% SDS (w/v) and 100 µg/ml denatured salmon sperm DNA with a probe concentration of ca. 2 ng/ml for 16 h at 65° C. followed by washes in 5×SSC at 65° C. (2×15 min), 2×SSC, 0.5% SDS (1×30 min), 0.2×SSC, 0.5% SDS (1×30 min), and 5×SSC (2×15 min). After autoradiography at −80° C. for 12 h, the probe #1 was removed from the filter according to the manufacturer's instructions and rehybridized with probe #2, and eventually with probe #3. The RNA ladder from Bethesda Research Laboratories was used as a size marker.

cDNA synthesis

First strand synthesis

Double-stranded cDNA was synthesized from 5 µg of *A. aculeatus* poly(A)$^+$ RNA by the RNase H method (Gubler & Hoffman 1983, Sambrook et al., 1989) using the hair-pin modification. The poly(A)$^+$RNA (5 µg in 5 µl of DEPC-treated water) was heated at 70° C. for 8 min., quenched on ice, and combined in a final volume of 50 µl with reverse transcriptase buffer (50 mM Tris-Cl, pH 8.3, 75 mM KCl, 3 mM MgC12, 10 mM DTT, Bethesda Research Laboratories) containing 1 mM each dNTP (Pharmacia), 40 units of human placental ribonuclease inhibitor (RNasin, Promega), 10 µg of oligo(dT)$_{12-18}$ primer (Pharmacia) and 1000 units of SuperScript II RNase H- reverse transcriptase (Bethesda Research Laboratories). First-strand cDNA was synthesized by incubating the reaction mixture at 45° C. for 1 h.

Second strand synthesis

After synthesis 30 µl of 10 mM Tris-Cl, pH 7.5, 1 mM EDTA was added, and the mRNA:cDNA hybrids were ethanol precipitated for 12 h at −20° C. by addition of 40 µg glycogen carrier (Boehringer Mannheim) 0.2 vols 10M NH$_4$Ac and 2.5 vols 96% EtOH. The hybrids were recovered by centrifugation, washed in 70% EtOH, air dried and resuspended in 250 µl of second strand buffer (20 mM Tris-Cl, pH 7.4, 90 mM KCl, 4.6 mM MgC12, 10 mM (NH$_4$)$_2$SO$_4$, 16 µM βNAD$^+$) containing 100 µM each dNTP, 44 units of *E. coli* DNA polymerase I (Amersham), 6.25 units of RNase H (Bethesda Research Laboratories) and 10.5 units of *E. coli* DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung bean nuclease treatment

The double-stranded (ds) cDNA was ethanol precipitated at −20° C. for 12 h by addition of 2 vols of 96% EtOH, 0.1 vol 3M NaAc, pH 5.2, recovered by centrifugation, washed in 70% EtOH, dried (SpeedVac), and resuspended in 30 µl of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 µl 10 mM Tris-Cl, pH 7.5, 1 mM EDTA, phenol extraction, and ethanol precipitation with 2 vols of 96% EtOH and 0.1 vol 3M NaAc, pH 5.2 at −20° C. for 12 h.

Blunt-ending with T4 DNA polymerase

The ds cDNA was blunt-ended with T4 DNA polymerase in 50 µl of T4 DNA polymerase buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at +37° C. for 15 min. The reaction was stopped by addition of EDTA to 20 mM final concentration, followed by phenol extraction and ethanol precipitation.

Adaptor ligation and size selection

After the fill-in reaction the cDNA was ligated to non-palindromic BstX I adaptors (1 µg/µl, Invitrogen) in 30 µl of ligation buffer (50 mM Tris-Cl, pH 7.8, 10 mM MgC12, 10 mM DTT, 1 mM ATP, 25 µg/ml bovine serum albumin) containing 600 pmol BstX I adaptors and 5 units of T4 ligase (Invitrogen) by incubating the reaction mix at +16° C. for 12 h. The reaction was stopped by heating at +70° C. for 5 min, and the adapted CDNA was size-fractionated by agarose gel electrophoresis (0.8% HSB-agarose, FMC) to separate unligated adaptors and small cDNAs. The cDNA was size-selected with a cut-off at 0.7 kb, and the CDNA was electroeluted from the agarose gel in 10 mM Tris-Cl, pH 7.5, 1 mM EDTA for 1 h at 100 volts, phenol extracted and ethanol precipitated at −20° C. for 12 h as above.

Construction of cDNA libraries

The adapted, ds CDNA was recovered by centrifugation, washed in 70% EtOH and resuspended in 25 ml DIW. Prior to large-scale library ligation, four test ligations were carried out in 10 µl of ligation buffer (same as above) each containing 1 µl ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector either pYES 2.0 vector Invitrogen or yHD13). The ligation reactions were performed by incubation at +16° C. for 12 h, heated at 70° C. for 5 min, and 1 µl of each ligation electroporated (200Ω, 2.5 kV, 25 µF) to 40 µl competent *E. coli* 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at +37° C. for 1 h , 50 µl plated on LB+ampicillin plates (100 µg/ml) and grown at +37° C. for 12 h.

Using the optimal conditions a large-scale ligation was set up in 40 µl of ligation buffer containing 9 units of T4 ligase, and the reaction was incubated at +16° C. for 12 h. The ligation reaction was stopped by heating at 70° C. for 5 min, ethanol. precipitated at −20 C. for 12 h, recovered by centrifugation and resuspended in 10 µl DIW. One µl aliquots were transformed into electrocompetent *E. coli* 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 µl of −80° C. bacterial stock propagated overnight.

Construction of yeast libraries

To ensure that all the bacterial clones were tested in yeast, a number of yeast transformants 5 times larger than the number of bacterial clones in the original pools was set as the limit.

One µl aliquots of purified plasmid DNA (100 ng/µl) from individual pools were electroporated (200 Ω, 1.5 kV, 25 µF) into 40 µl competent *S. cerevisiae* JG 169 cells (OD600=1.5 in 500 ml YPD, washed twice in cold DIW, once in cold 1M sorbitol, resuspended in 0.5 ml 1M sorbitol, Becker & Guarante, 1991). After addition of 1 ml 1M cold sorbitol, 80

µl aliquots were plated on SC+glucose-uracil to give 250–400 c.f.u./plate and incubated at 30° C. for 3–5 days.

Construction of an Aspergillus expression vector

The vector pHD414 is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3' end of the terminator, and subsequent removal of an approximately 250 bp long fragment at the 5' end of the promoter, also containing undesirable sites. The 200 bp region was removed by cleavage with NarI (positioned in the pUC vector) and XbaI (just 3' to the terminator), subsequent filling in the generated ends with Klenow DNA polymerase +dNTP, purification of the vector fragment on gel and religation of the vector fragment. This plasmid was called pHD413. pHD413 was cut with StuI (positioned in the 5' end of the promoter) and PvuII (in the pUC vector), fractionated on gel and religated. The plasmid pHD 414 is shown in FIG. 2.

Media

YPD 10 g yeast extract, 20 g peptone, $H_2O$ to 810 ml. Autoclaved, 90 ml 20% glucose (sterile filtered) added.

10×Basal salt: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophan, $H_2O$ ad 806 ml, autoclaved, 3.6 ml 5% threonine and 90 ml 20% glucose or 20% galactose added.

SC-H broth 7.5 g/l yeast nitrogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.

SC-H agar 7.5 g/l yeast nitrogen base without amino acids, 11.3 g/l succinic acid, 6.8 g/l NaOH, 5.6 g/l casamino acids without vitamins, 0.1 g/l tryptophan, and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth

Composition as YNB-1 agar, but without the agar.

FG-4-Agar 35 g/L agar, 30 g/L Soy bean meal, 15 g/L maltodextrin (Glucidex 6), 5 g/L Bacto pepton, pH 7. Autoclaved 40 min at 121° C.

FG-4 medium 30 g/L Soy bean meal, 15 g/L maltodextrin (Glucidex 6), 5 g/L Bacto peptone. Autoclaved 40 min at 121° C.

MDU-2 medium 45 g/L maltose, 1 g/L $MgSO_4$—7 $H_2O$, 1 g/L NaCl, 2g/L $K_2SO_4$, 12 g/L $KH_2PO_4$, 0.1 ml/L Pluronic 61L, 0.5 ml/L Trace metal solution. pH 5.0. Autoclaved 20 min at 121° C. 15 ml/L 50% sterile filtered urea is added after autoclaving.

AZCL galactomannan: available from Megazyme, Australia.

Transformation of Aspergillus oryzae or Aspergillus niger (general procedure)

100 ml of YPD (Sherman et al., Methods in Yeast Genetics, Cold Spring Harbor Laboratory, 1981) is inoculated with spores of A. oryzae or A. niger and incubated with shaking at 37° C. for about 2 days. The mycelium is harvested by filtration through miracloth and washed with 200 ml of 0.6M $MgSO_4$. The mycelium is suspended in 15 ml of 1.2M $MgSO_4$, 10 mM $NaH_2PO_4$, pH=5.8. The suspension is cooled on ice and 1 ml of buffer containing 120 mg of Novozymo® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH=7.0. Centrifugation is performed for 15 minutes at 100 g and the protoplasts are collected from the top of the $MgSO_4$ cushion. 2 volumes of STC (1.2M sorbitol, 10 mM Tris-HCl, pH=7.5, 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 µl of protoplast suspension is mixed with 5–25 µg of the appropriate DNA in 10 µl of STC. Protoplasts are mixed with p3SR2 (an A. nidulans amdS gene carrying plasmid). The mixture is left at room temperature for 25 minutes. 0.2 ml of 60% PEG 4000 (BDH 29576), 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove Biochem. Biophys. Acta 113 (1966) 51–56) containing 1.0M sucrose, pH =7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Fed batch fermentation

Fed batch fermentation was performed in a medium comprising maltodextrin as a carbon source, urea as a nitrogen source and yeast extract. The fed batch fermentation was performed by innoculating a shake flask culture of A. oryzae host cells in question into a medium comprising 3.5% of the carbon source and 0.5% of the nitrogen source. After 24 hours of cultivation at pH 5.0 and 34° C. the continuous supply of additional carbon and nitrogen sources were initiated. The carbon source was kept as the limiting factor and it was secured that oxygen was present in excess. The fed batch cultivation was continued for 4 days, after which the enzymes could be recovered by centrifugation, ultrafiltration, clear filtration and germ filtration.

Purification of the recombinant µ-1,4-mannanase 50 ml of culture supernatant was harvested after 3 days of culture, and concentrated on a 20 $cm^2$ 10 kDa Amicon ultrafiltration device into 20 mM Tris pH 8.0. This material was loaded on a Fast-Flow Q-Sepharose HR 16/20 column (Pharmacia, Sweden) at 1.5 ml/min, and eluted with a linear NaCl gradient (from 0 to 0.4M NaCl). The enzyme eluted at approx. 0.15M NaCl, and was further purified by gel-filtration on a HR 26/200 Sephacryl S-200 column (Pharmacia, Sweden) in 0.25M ammonium acetate pH 5.5 at 1 ml/min. Protein quantity was measured by the BioRad protein assay (BioRad, USA).

Electrophoresis

SDS-PAGE electrophoresis was performed in a Mini-Leak 4 electrophoresis unit (Kem-En-Tec, Denmark) as a modified version of the Laemli procedure (Laemmli 1970). Isoelectric focusing was carried out on Ampholine PAG plates pH 3.5–9.5 (Pharmacia, Sweden) on a Multiphor electrophoresis unit according to the manufactures instructions. Gels were either silverstained essentially as described in (Merrild, Switzer et al. 1979) or coomassie stained according to (Matsudaira 1989).

Assay of mannanase activity 0.4% suspensions of AZCL-mannan (Megazyme, Australia) were mixed 1:1 with 0.1M buffer (Sodium citrate/tri-Sodium phosphate), enzyme was added, and the incubations were carried out at 30° C. for 15 min, followed by inactivation of the enzyme at 95° C. for 20 min. After centrifugation the release of blue color into the supernatant was measured in microtiter plates at β0 nm. For determination of pH optima, the enzymatic reaction was carried out in citrate/phosphate buffers from pH 2.5 to 9. For determination of temperature optimum, the enzyme was incubated at pH 5.0 with substrate at temperatures from 300° to 80° C. $K_m$ and specific activity was measured by carrying out incubations in 0.1M citrate buffer pH 5.0 at substrate concentrations ranging from 0.025 to 1% carob galactomannan (Megazyme, Austrailia). The results were plotted in a "Hanes plot" where the slope is $1/V_{max}$ and the intercept is $K_m/V_{max}$.

EXAMPLE 1

A library from A. aculeatus consisting of approx. $1.5 \times 10^6$ individual clones in 150 pools was constructed.

DNA was isolated from 20 individual clones from the library and subjected to analysis for cDNA insertion. The insertion frequency was found to be >90% and the average insert size was approximately 1400 bp.

DNA from some of the pools was transformed into yeast, and 50–100 plates containing 200–500 yeast colonies were obtained from each pool. After 3–5 days of growth, the agar plates were replica plated onto several sets of agar plates. One set of plates containing 0.1% AZCL galactomannan (Megazyme), was then incubated for 3–5 days at 30° C. for detection of mannanase activity. Positive colonies were identified as colonies surrounded by a blue halo. Alternatively, one set of plates was incubated for 3–5 days at 30° C. before overlayering with a mannan overlayer gel containing 0.1% AZCL galactomannan and 1% agarose in a buffer with an appropriate pH. After incubation for 1–2 days at 30° C., positive colonies were identified as colonies surrounded by a blue halo.

Cells from enzyme-positive colonies were spread for single colony isolation on agar, and an enzyme-producing single colony was selected for each of the mannanase-producing colonies identified.

Characterization of positive clones

The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical). The cDNA sequence encoding the entire enzyme is shown in SEQ ID No. 1.

Isolation of a CDNA gene for expression in Aspergillus

One or more of the mannanase-producing colonies were inoculated into 20 ml YNB-1broth in a 50 ml glass test tube. The tube was shaken for 2 days at 30° C. The cells were harvested by centrifugation for 10 min. at 3000 rpm.

The cells were resuspended in 1 ml 0.9M sorbitol, 0.1M EDTA, pH 7.5. The pellet was transferred to an Eppendorf tube, and spun for 30 seconds at full speed. The cells were resuspended in 0.4 ml 0.9M sorbitol, 0.1M EDTA, 14 mM β-mercaptoethanol, 100 µl 2 mg/ml Zymolase was added, and the suspension was incubated at 37° C. for 30 minutes and spun for 30 seconds. The pellet (spheroplasts) was resuspended in 0.4 ml TE. 90 µl of (1.5 ml 0.5M EDTA pH 8.0, 0.6 ml 2M Tris-Cl pH 8.0, 0.6 ml 10% SDS) was added, and the suspension was incubated at 65° C. for 30 minutes. 80 µl 5M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% ETOH, spun for 30 seconds and dried at room temperature. The pellet was resuspended in 50 µl TE and spun for 15 minutes. The supernatant was transferred to a fresh tube. 2.5 µl 10 mg/ml RNase was added, followed by incubation at 37° C. for 30 minutes and addition of 500 µl isopropanol with gentle mixing. The mixture was spun for 30 seconds, and the supernatant was removed. The pellet was rinsed with cold 96% EtOH and dried at room temperature. The DNA was dissolved in 50 µl water to a final concentration of approximately 100 µl/ml.

The DNA was transformed into E. coli by standard procedures. Two E. coli colonies were isolated from each of the transformations and analysed with the restriction enzymes HindIII and XbaI which excised the DNA insert. DNA from one of these clones was retransformed into yeast strain JG169.

The DNA sequences of several of the positive clones were determined. The entire DNA sequence is shown in SEQ ID No. 1, a partial DNA sequence of a mannanase is shown in SEQ ID No. 3.

EXAMPLE 2

Expression of mannanase

In order to express the genes in Aspergillus, cDNA is isolated from one or more representatives of each family by digestion lo with HindIII/XbaI or other appropriate restriction enzymes, size fractionation on a gel and purification and subsequently ligated to pHD414, resulting in the plasmid pA1M3. After amplification in E. coli , the plasmids are transformed into A. oryzae or A. niger according to the general procedure described is above.

Test of A. oryzae transformants

Each of the transformants was inoculated in the center of a Petri dish with FG-4 agar. After 5 days of incubation at 30° C. 4 mm diameter plugs were removed from the center of the colonies by a corkscrew. The plugs were embedded in a mannan overlayer gel, containing 0.1% AZCL galactomannan and 1% agarose in a buffer with an appropriate pH, and incubated overnight at 40° C. The mannanase activity was identified as described above. Some of the transformants had halos which were significantly larger than the Aspergillus oryzae background. This demonstrates efficient expression of mannanase in Aspergillus oryzae. The 8 transformants with the highest mannanase activity were selected and inoculated and maintained on YPG-agar.

Each of the 8 selected transformants were inoculated from YPG-agar slants on 500 ml shake flask with FG-4 and MDU-2 media. After 3–5 days of fermentation with sufficient agitation to ensure good aeration, the culture broths were centrifuged for 10 minutes at 2000 g and the supernatants were analyzed.

A volume of 15 μl of each supernatant was applied to 4 mm diameter holes punched out in a 0.1% AZCL galactomannan overlayer gel (25 ml in a 13 cm diameter Petri dish). The mannanase activity was identified by the formation of a blue halo on incubation.

Subsequently, the mannanase was produced by fed batch fermentation of *A. oryzae* expressing the enzyme as described in Materials and Methods above.

EXAMPLE 3
Purification and characterization of recomb. mannanase

The recombinant mannanase enzyme produced by the method described above was purified from the culture supernatant by the two step procedure described in the Materials and Methods section above involving a first step of anion exchange chromatography followed by gel-filtration. This procedure yielded an enzyme preparation of more than 95% purity as determined by SDS-PAGE electrophoresis.

The purified recombinant enzyme was characterized with regard to molecular weight, isoelectric point, pH optimum, temperature optimum, pH & temperature stability and Km and specific activity (table 1). The enzyme had a relatively broad pH optimum, and was active and stable at temperatures up to 70° C. (table 1 and FIG. 3). These properties may facilitate the use of the enzyme in a wide variety of industrial processes.

TABLE 1

| Enzymatic characteristics of the purified recombinant mannanase from *A. aculeatus* expressed in *A. oryzae*. | |
|---|---|
| Characteristics | β-1,4-mannanase |
| MW | 45.000 Da |
| pI | 4.5 |
| pH optimum | pH 5.0 |
| temperature optimum | 60–70° C. |
| pH stability | pH 2.5–10.0 |
| temperature stability | <70° C. |
| $K_m$ | 0.07% carob galactomannan |
| Specific activity | 60 μmol/min · mg enzyme |

For comparison the calculated Mw of the enzyme was 41.000 KDa and the calculated pI 4.7 indicating that the recombinant enzyme is glycosylated.

The recombinant mannanase was found to bind GNA lectin (from *Giganthus nivalis*) specific for high mannose N-linked glycosylation with terminal mannose, indicating the presence of this type of glycosylation (data not showed). The enzyme has a number of potential N-glycosylation sites but it was not determined which of these sites served as attachment for the glycan moieties.

The cloning of a β-1,4-mannanase described in the present application makes it possible to express this enzyme in large amounts essentially free from other polysaccharide degrading enzymes. Such a monocomponent enzyme preparation may be of great value for modification and processing of various mannan containing gums as well as other mannan containg biological materials.

REFERENCES CITED IN THE SPECIFICATION

Aviv, H. & Leder, P. 1972. Proc. Natl. Acad. Sci. U. S. A. 69: 1408–1412.

Becker, D. M. & Guarante, L. 1991. Methods Enzymol. 194: 182–187.

Chirgwin, J. M., Przybyla, A. E., MacDonald, R. J. & Rutter, W. J. 1979. Biochemistry 18: 5294–5299.

Gubler, U. & Hoffman, B. J. 1983. Gene 25: 263–269.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U. S. A. 74: 5463–5467.

Araujo, A. and O. P. Ward (1990). "Extracellular mannanases and galactanases from selected fungi." *J. Ind. Microbiol.* 6: 171–178.

Araujo, A. and O. P. Ward (1990). "Hemicellulases of bacillus species: preliminary comparative studies on production and properties of mannanases and galactanases." *J. Appl. Bacteriol.* 68: 253–261.

Arcand, N., D. Kluepfel, et al. (1993). "β-Mannanase of *Streptomyces lividans* 66: cloning and DNA sequence of the manA gene and characterization of the enzyme." *Biochem. J.* 290: 857–863.

Arisan-Atac, I., R. Hodtis, et al. (1993). "Purification and characterization of a β-mannanase of *Trichoderma reesei* C-30."

Dalbøge, H. and H. Heldt-Hansen (1994). "A novel method for efficient expression cloning of fungal enzyme genes." *Mol. Gen. Genet.* in press:

Dekker, R. F. H. . (1979). The Hemicellulase Group of Enzymes. *Polysaccharides in Food*. London, Butterworths.

Gibbs, M. D., D. J. Saul, et al. (1992). "The β-mannanase from *caldocellum saccharolyticum* is part of a multidomain enzyme." *Appl. Environment. Microbiol.* 58: 3864–3867.

Henrissat, B. (1993). "Hidden domains and active-site residues in beta-glycanase-encoding gene-sequences." *GENE* 125: 199–204.

Johnson, K. G. (1990). "Exocellular β-mannanases from hemicellulytic fungi." *World J. Microbiol. Biotechnol.* 6: 209–217.

Laemmli, U. K. (1970). "Cleavage of structural proteins during the assembly of the head of bacteriophage T4." *Nature* 227: 680–685.

Matsudaira, P. T., Ed. (1989). *A practical guide to protein and peptide purification for microseguencing*. San Diego, Academic Press Inc.

McCleary, B. V. (1988). "Carob and guar galactomannans." *Meth Enzymol* 160: 523–527.

McCleary, B. V. (1988). "β-D-Mannanase." *Meth. Enzymol.* 160: 596–610.

Merrild, C. R., R. C. Switzer, et al. (1979). *Proc. Natl. Acad. Sci. USA* 76: 4335–4339.

We claim:

1. An isolated and purified DNA molecule encoding a mannanase enzyme having the amino acid sequence of SEQ ID NO:2.

2. The isolated and purified DNA molecule of claim 1, comprising the DNA sequence of SEQ ID NO:1.

3. A recombinant expression vector containing the DNA sequence of claim 1.

4. A host cell containing the vector of claim 3.

5. The host cell of claim 4, wherein said cell is a eukaryotic cell.

6. The eukaryotic cell of claim 5, wherein said cell is selected from the group consisting of a yeast cell or a filamentous fungal cell.

7. The cell of claim 6, wherein said cell is an Aspergillus cell.

8. The cell of claim 7, wherein said Aspergillus cell is *Aspergillus niger* or *Aspergillus oryzae*.

9. A method of producing an enzyme exhibiting mannanase activity, the method comprising culturing the host cell of claim 4 under conditions permitting the production of the enzyme, and recovering the enzyme from the culture.

* * * * *

SEQUENCE LISTING ( 1 ) GENERAL INFORMATION:

( i i i ) NUMBER OF SEQUENCES: 15

( 2 ) INFORMATION FOR SEQ ID NO: 1:

( i ) SEQUENCE CHARACTERISTICS:
        ( A ) LENGTH: 1302 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION:61..1192

( x i ) SEQUENCE DESCRIPTION: SEQ ID NO: 1:

```
GGATCCACTA GTAACGGCCG CCAGTGTGGT GGAATTCCTC GACACCACCA CACAACCAAG    60

ATG AAG CTT TCT CAC ATG CTC CTC AGC CTC GCC AGC CTG GGG GTG GCG    108
Met Lys Leu Ser His Met Leu Leu Ser Leu Ala Ser Leu Gly Val Ala
 1           5                  10                  15

ACG GCT CTT CCC CGG ACG CCG AAC CAC AAC GCG GCC ACC ACC GCC TTC    156
Thr Ala Leu Pro Arg Thr Pro Asn His Asn Ala Ala Thr Thr Ala Phe
            20                  25                  30

CCC AGC ACC TCG GGG CTG CAC TTC ACG ATT GAC GGC AAG ACG GGC TAC    204
Pro Ser Thr Ser Gly Leu His Phe Thr Ile Asp Gly Lys Thr Gly Tyr
        35                  40                  45

TTT GCC GGG ACC AAC TCG TAC TGG ATC GGG TTC CTG ACC AAC AAC GAC    252
Phe Ala Gly Thr Asn Ser Tyr Trp Ile Gly Phe Leu Thr Asn Asn Asp
    50                  55                  60

GAC GTG GAC CTC GTC ATG AGC CAG CTG GCG GCA TCC GAC CTC AAG ATC    300
Asp Val Asp Leu Val Met Ser Gln Leu Ala Ala Ser Asp Leu Lys Ile
65                  70                  75                  80

CTG CGG GTC TGG GGG TTC AAC GAC GTC AAC ACC AAG CCC ACC GAC GGG    348
Leu Arg Val Trp Gly Phe Asn Asp Val Asn Thr Lys Pro Thr Asp Gly
                85                  90                  95

ACG GTG TGG TAC CAG CTG CAC GCG AAC GGC ACC TCG ACC ATC AAC ACG    396
Thr Val Trp Tyr Gln Leu His Ala Asn Gly Thr Ser Thr Ile Asn Thr
            100                 105                 110

GGC GCG GAC GGG CTC CAG CGC CTC GAC TAC GTG GTG ACC TCG GCC GAG    444
Gly Ala Asp Gly Leu Gln Arg Leu Asp Tyr Val Val Thr Ser Ala Glu
        115                 120                 125

AAG TAC GGC GTC AAG CTG ATC ATC AAC TTC GTC AAC GAG TGG ACC GAC    492
Lys Tyr Gly Val Lys Leu Ile Ile Asn Phe Val Asn Glu Trp Thr Asp
    130                 135                 140

TAC GGC GGC ATG CAG GCC TAC GTC ACG GCC TAC GGC GCC GCC GCC CAG    540
Tyr Gly Gly Met Gln Ala Tyr Val Thr Ala Tyr Gly Ala Ala Ala Gln
145                 150                 155                 160

ACG GAC TTC TAC ACC AAC ACC GCC ATC CAG GCC GCC TAC AAG AAC TAC    588
Thr Asp Phe Tyr Thr Asn Thr Ala Ile Gln Ala Ala Tyr Lys Asn Tyr
                165                 170                 175

ATC AAG GCG GTC GTC TCG CGG TAC AGC AGC TCC GCC GCC ATC TTC GCC    636
Ile Lys Ala Val Val Ser Arg Tyr Ser Ser Ser Ala Ala Ile Phe Ala
            180                 185                 190

TGG GAG CTG GCC AAC GAG CCC CGC TGC CAG GGC TGC GAT ACC TCG GTC    684
Trp Glu Leu Ala Asn Glu Pro Arg Cys Gln Gly Cys Asp Thr Ser Val
        195                 200                 205

CTG TAC AAC TGG ATC TCG GAC ACG TCC AAG TAT ATC AAG TCG CTG GAC    732
Leu Tyr Asn Trp Ile Ser Asp Thr Ser Lys Tyr Ile Lys Ser Leu Asp
    210                 215                 220
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| TCC | AAG | CAC | CTG | GTC | ACG | ATT | GGC | GAT | GAG | GGC | TTC | GGT | CTC | GAC | GTC | 780  |
| Ser | Lys | His | Leu | Val | Thr | Ile | Gly | Asp | Glu | Gly | Phe | Gly | Leu | Asp | Val |      |
| 225 |     |     |     |     | 230 |     |     |     | 235 |     |     |     |     |     | 240 |      |
| GAC | TCC | GAC | GGC | AGC | TAC | CCC | TAC | ACC | TAC | GGC | GAG | GGA | TTG | AAC | TTC | 828  |
| Asp | Ser | Asp | Gly | Ser | Tyr | Pro | Tyr | Thr | Tyr | Gly | Glu | Gly | Leu | Asn | Phe |      |
|     |     |     |     | 245 |     |     |     |     | 250 |     |     |     |     | 255 |     |      |
| ACC | AAG | AAC | CTG | GGC | ATC | TCG | ACC | ATC | GAC | TTC | GGT | ACT | CTG | CAT | CTG | 876  |
| Thr | Lys | Asn | Leu | Gly | Ile | Ser | Thr | Ile | Asp | Phe | Gly | Thr | Leu | His | Leu |      |
|     |     |     | 260 |     |     |     |     | 265 |     |     |     |     | 270 |     |     |      |
| TAC | CCC | GAT | AGC | TGG | GGC | ACC | TCC | TAC | GAC | TGG | GGC | AAC | GGC | TGG | ATC | 924  |
| Tyr | Pro | Asp | Ser | Trp | Gly | Thr | Ser | Tyr | Asp | Trp | Gly | Asn | Gly | Trp | Ile |      |
|     |     | 275 |     |     |     |     | 280 |     |     |     |     | 285 |     |     |     |      |
| ACG | GCC | CAC | GCG | GCC | GCC | TGC | AAG | GCG | GTG | GGC | AAG | CCG | TGC | CTG | CTG | 972  |
| Thr | Ala | His | Ala | Ala | Ala | Cys | Lys | Ala | Val | Gly | Lys | Pro | Cys | Leu | Leu |      |
|     | 290 |     |     |     | 295 |     |     |     |     | 300 |     |     |     |     |     |      |
| GAA | GAG | TAC | GGA | GTG | ACC | TCC | AAC | CAC | TGT | GCC | GTC | GAG | AGC | CCC | TGG | 1020 |
| Glu | Glu | Tyr | Gly | Val | Thr | Ser | Asn | His | Cys | Ala | Val | Glu | Ser | Pro | Trp |      |
| 305 |     |     |     |     | 310 |     |     |     | 315 |     |     |     |     |     | 320 |      |
| CAG | CAG | ACG | GCC | GGC | AAC | GCG | ACG | GGC | ATC | TCC | GGC | GAT | TTG | TAC | TGG | 1068 |
| Gln | Gln | Thr | Ala | Gly | Asn | Ala | Thr | Gly | Ile | Ser | Gly | Asp | Leu | Tyr | Trp |      |
|     |     |     |     | 325 |     |     |     |     | 330 |     |     |     |     | 335 |     |      |
| CAG | TAT | GGC | ACC | ACG | TTC | AGC | TGG | GGC | CAG | TCC | CCG | AAC | GAT | GGG | AAC | 1116 |
| Gln | Tyr | Gly | Thr | Thr | Phe | Ser | Trp | Gly | Gln | Ser | Pro | Asn | Asp | Gly | Asn |      |
|     |     |     | 340 |     |     |     |     | 345 |     |     |     |     | 350 |     |     |      |
| ACC | TTC | TAC | TAC | AAC | ACC | AGC | GAC | TTC | ACG | TGC | CTG | GTG | ACG | GAT | CAT | 1164 |
| Thr | Phe | Tyr | Tyr | Asn | Thr | Ser | Asp | Phe | Thr | Cys | Leu | Val | Thr | Asp | His |      |
|     |     | 355 |     |     |     |     | 360 |     |     |     |     | 365 |     |     |     |      |
| GTG | GCG | GCC | ATC | AAT | GCG | CAG | TCG | AAG | T AGACTGTTGG CGTGGTGGAA |     |     |     |     |     |     | 1212 |
| Val | Ala | Ala | Ile | Asn | Ala | Gln | Ser | Lys |     |     |     |     |     |     |     |      |
|     | 370 |     |     |     |     | 375 |     |     |     |     |     |     |     |     |     |      |

GGAACAAGTA GCCTTAGTAT AGGGTTAGCA AATGATTGCG GTGGAGAGAA CAAATAAAAT   1272

GGTGGTCAAT GATTATCGCG AAAAAAAAAA   1302

( 2 ) INFORMATION FOR SEQ ID NO: 2:

( i ) SEQUENCE CHARACTERISTICS:
        ( A ) LENGTH: 377 amino acids
        ( B ) TYPE: amino acid
        ( D ) TOPOLOGY: linear ( x i ) SEQUENCE DESCRIPTION: SEQ ID NO: 2:

| Met | Lys | Leu | Ser | His | Met | Leu | Leu | Ser | Leu | Ala | Ser | Leu | Gly | Val | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Thr | Ala | Leu | Pro | Arg | Thr | Pro | Asn | His | Asn | Ala | Ala | Thr | Thr | Ala | Phe |
|     |     |     | 20  |     |     |     |     | 25  |     |     |     |     | 30  |     |     |
| Pro | Ser | Thr | Ser | Gly | Leu | His | Phe | Thr | Ile | Asp | Gly | Lys | Thr | Gly | Tyr |
|     |     |     | 35  |     |     |     | 40  |     |     |     |     | 45  |     |     |     |
| Phe | Ala | Gly | Thr | Asn | Ser | Tyr | Trp | Ile | Gly | Phe | Leu | Thr | Asn | Asn | Asp |
|     | 50  |     |     |     |     | 55  |     |     |     |     | 60  |     |     |     |     |
| Asp | Val | Asp | Leu | Val | Met | Ser | Gln | Leu | Ala | Ala | Ser | Asp | Leu | Lys | Ile |
| 65  |     |     |     |     | 70  |     |     |     |     | 75  |     |     |     |     | 80  |
| Leu | Arg | Val | Trp | Gly | Phe | Asn | Asp | Val | Asn | Thr | Lys | Pro | Thr | Asp | Gly |
|     |     |     |     | 85  |     |     |     |     | 90  |     |     |     |     | 95  |     |
| Thr | Val | Trp | Tyr | Gln | Leu | His | Ala | Asn | Gly | Thr | Ser | Thr | Ile | Asn | Thr |
|     |     |     | 100 |     |     |     |     | 105 |     |     |     |     | 110 |     |     |
| Gly | Ala | Asp | Gly | Leu | Gln | Arg | Leu | Asp | Tyr | Val | Val | Thr | Ser | Ala | Glu |
|     |     |     | 115 |     |     |     | 120 |     |     |     |     | 125 |     |     |     |
| Lys | Tyr | Gly | Val | Lys | Leu | Ile | Ile | Asn | Phe | Val | Asn | Glu | Trp | Thr | Asp |
|     |     | 130 |     |     |     |     | 135 |     |     |     | 140 |     |     |     |     |

Tyr Gly Gly Met Gln Ala Tyr Val Thr Ala Tyr Gly Ala Ala Ala Gln
145                 150                 155                 160

Thr Asp Phe Tyr Thr Asn Thr Ala Ile Gln Ala Ala Tyr Lys Asn Tyr
                165                 170                 175

Ile Lys Ala Val Val Ser Arg Tyr Ser Ser Ala Ala Ile Phe Ala
            180                 185                 190

Trp Glu Leu Ala Asn Glu Pro Arg Cys Gln Gly Cys Asp Thr Ser Val
        195                 200                 205

Leu Tyr Asn Trp Ile Ser Asp Thr Ser Lys Tyr Ile Lys Ser Leu Asp
    210                 215                 220

Ser Lys His Leu Val Thr Ile Gly Asp Glu Gly Phe Gly Leu Asp Val
225                 230                 235                 240

Asp Ser Asp Gly Ser Tyr Pro Tyr Thr Tyr Gly Glu Gly Leu Asn Phe
            245                 250                 255

Thr Lys Asn Leu Gly Ile Ser Thr Ile Asp Phe Gly Thr Leu His Leu
            260                 265                 270

Tyr Pro Asp Ser Trp Gly Thr Ser Tyr Asp Trp Gly Asn Gly Trp Ile
        275                 280                 285

Thr Ala His Ala Ala Ala Cys Lys Ala Val Gly Lys Pro Cys Leu Leu
    290                 295                 300

Glu Glu Tyr Gly Val Thr Ser Asn His Cys Ala Val Glu Ser Pro Trp
305                 310                 315                 320

Gln Gln Thr Ala Gly Asn Ala Thr Gly Ile Ser Gly Asp Leu Tyr Trp
            325                 330                 335

Gln Tyr Gly Thr Thr Phe Ser Trp Gly Gln Ser Pro Asn Asp Gly Asn
            340                 345                 350

Thr Phe Tyr Tyr Asn Thr Ser Asp Phe Thr Cys Leu Val Thr Asp His
        355                 360                 365

Val Ala Ala Ile Asn Ala Gln Ser Lys
370                 375

( 2 ) INFORMATION FOR SEQ ID NO:3:

( i ) SEQUENCE CHARACTERISTICS:
( A ) LENGTH: 248 base pairs
( B ) TYPE: nucleic acid
( C ) STRANDEDNESS: single
( D ) TOPOLOGY: linear ( x i ) SEQUENCE DESCRIPTION: SEQ ID NO:3:

| | | | | | |
|---|---|---|---|---|---|
| CTCGACACCA | CCACACAACC | AAGATGAAGC | TTTCTCACAT | GCTCCTCAGC | CTCGCCAGCC | 60 |
| TGGGGGTGGC | GACGGCTCTT | CCCCGGACGC | CGAACCACAA | CGCGGCCACC | ACCGCCTTCC | 120 |
| CCAGCACCTC | GGGGCTGCAC | TTCACGATTG | ACGGCAAGAC | GGGCTACTTT | GCCGGGACCA | 180 |
| ACTCGTACTG | GATCGGGTTC | CTGACCAACA | ACGACGACGT | GGACCTCGTC | ATGAGCCAGC | 240 |
| TGGCGCAT | | | | | | 248 |

( 2 ) INFORMATION FOR SEQ ID NO:4:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:4:

CTCGACACCA   CCACACAACC                                                    20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

AAGATGAAGC TTTCTCACAT         20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

GCTCCTCAGC CTCGCCAGCC         20

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TGGGGGTGGC GACGGCTCTT C         21

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

CCCGGACGCC GAACCACAAC         20

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GCGGCCACCA CCGCCTTCCC         20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

CAGCACCTCG GGGCTGCACT         20

( 2 ) INFORMATION FOR SEQ ID NO:11:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:11:

TCACGATTGA CGGCAAGACG        20

( 2 ) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:12:

GGCTACTTTG CCGGGACCAA        20

( 2 ) INFORMATION FOR SEQ ID NO:13:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:13:

CTCGTACTGG ATCGGGTTCC        20

( 2 ) INFORMATION FOR SEQ ID NO:14:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

TGACCAACAA CGACGACGTG        20

( 2 ) INFORMATION FOR SEQ ID NO:15:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

GACCTCGTCA TGAGCCAGCT GGCGCAT        27